United States Patent
Isaksen

(10) Patent No.: US 7,801,274 B1
(45) Date of Patent: *Sep. 21, 2010

(54) DIGITAL DENTAL IMAGE APPARATUS HAVING LOW NOISE POWER SUPPLY SYSTEM

(75) Inventor: David B. Isaksen, Mountain View, CA (US)

(73) Assignee: Wideband Semiconductors, Inc., Mountain View, CA (US)

( * ) Notice: Subject to any disclaimer, the term of this patent is extended or adjusted under 35 U.S.C. 154(b) by 16 days.

This patent is subject to a terminal disclaimer.

(21) Appl. No.: 12/231,368

(22) Filed: Sep. 2, 2008

Related U.S. Application Data

(63) Continuation-in-part of application No. 11/142,179, filed on May 31, 2005, now Pat. No. 7,453,986.

(51) Int. Cl.
*H05G 1/64* (2006.01)
(52) U.S. Cl. .............................. 378/98; 378/38; 378/98.8
(58) Field of Classification Search ................... 378/38, 378/91, 98, 98.2, 98.8, 191
See application file for complete search history.

(56) References Cited

U.S. PATENT DOCUMENTS

| 6,134,298 | A | 10/2000 | Schick et al. |
| 6,404,854 | B1 * | 6/2002 | Carroll et al. ............... 378/98.8 |
| 7,453,986 | B1 * | 11/2008 | Isaksen ........................ 378/98 |

\* cited by examiner

*Primary Examiner*—Jurie Yun
(74) *Attorney, Agent, or Firm*—Boris G. Tankhilevich

(57) ABSTRACT

A digital dental image apparatus comprising: an intra-oral image sensor configured to output a raw analog video signal; a processing raw analog video signal (PRAVS) means for processing the raw analog video signal for optimum detection; a digitizing, over sampling, and averaging (DOSA) means for digitizing, over sampling, and averaging the optimized analog video signal; a programmable control and signal processing (PCSP) means configured to generate a control signal to control an over sampling rate of the (DOSA) means; and a low noise power supply that improves the intra-oral image sensor performance. The PCSP means is configured to process the DOSA video signal, and configured to output the processed DOSA video signal to an output network interface.

26 Claims, 11 Drawing Sheets

Noise Shaping

Noise Shaping

A/D Level Out
Dental Video from X-ray

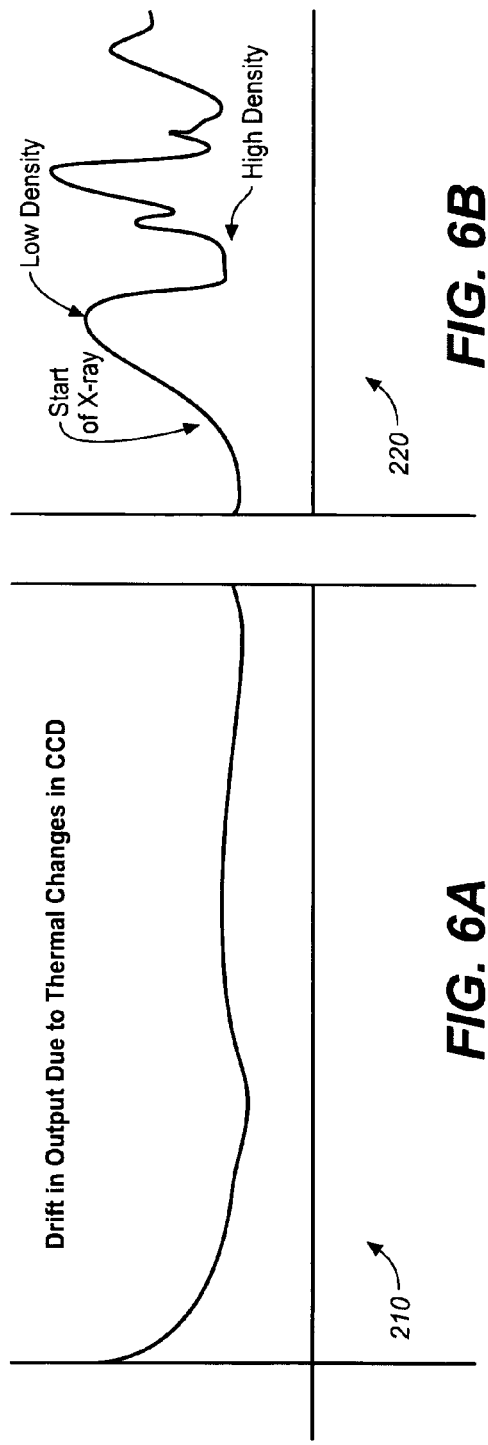
FIG. 6A
FIG. 6B
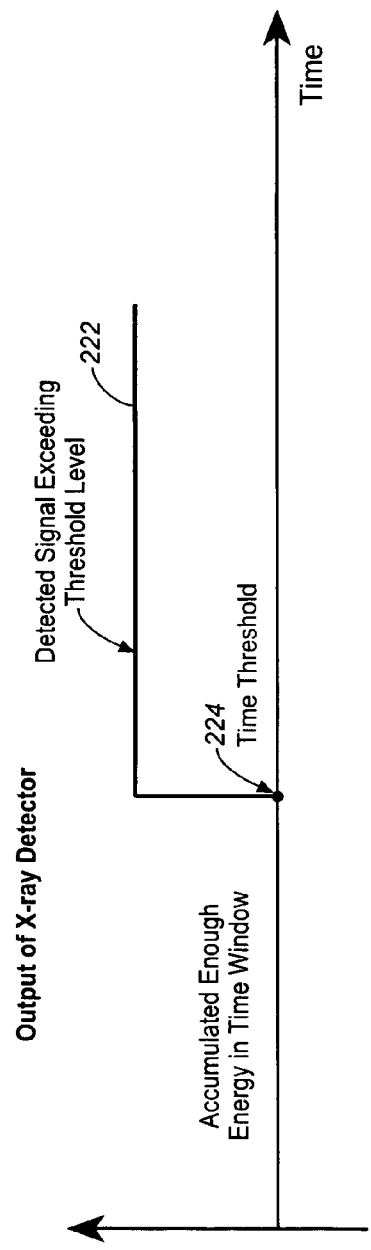
FIG. 6C

DIGITAL DENTAL IMAGE APPARATUS HAVING LOW NOISE POWER SUPPLY SYSTEM

This is a continuation-in-part patent application claiming priority of the U.S. patent application Ser. No. 11/142,179, filed on May 31, 2005, now U.S. Pat. No. 7,453,986 and entitled "DIGITAL DENTAL IMAGE APPARATUS".

TECHNICAL FIELD

The technology relates to the field digital dental image apparatus.

BACKGROUND

In the prior art film less dental radiography, an X-ray beam is projected through the patient's tooth, but no photographic film is used. Instead, an electronic sensor is placed in the patient's mouth behind the tooth to be examined. The electronic sensor may include a charge-coupled device (CCD), an active pixel sensor (APS) array or any other film less radiation sensor. The X-rays pass through the tooth and impinge on the electronic sensor, which converts the X-rays into an electrical signal. The electrical signal is transmitted over a wire to a computer, either directly or through a module including intermediate processing circuitry. The computer then processes the signal to produce an image on an associated output device, such as a monitor or a printer.

However, in the prior art filmless dental radiography the noise level can be high enough and it is difficult to filter it out without extensive or expensive circuitry.

SUMMARY

This Summary is provided to introduce a selection of concepts that are further described below in the Detailed Description. This Summary is not intended to identify key or essential features of the claimed subject matter, nor is it intended to be used as an aid in determining the scope of the claimed subject matter.

The digital dental image apparatus is provided. The apparatus comprises: an intra-oral image sensor configured to output a raw analog video signal, a processing raw analog video signal (PRAVS) means for processing the raw analog video signal for optimum detection, a digitizing, over sampling, and averaging (DOSA) means for digitizing, over sampling, and averaging the optimized analog video signal, a programmable control and signal processing (PCSP) means; and a power supply selected from the group consisting of: {a rechargeable battery, a large capacitor including a charger; and a Low Voltage Dropout (LDO) power supply}.

The PRAVS means is configured to output an optimized analog video signal. The DOSA means is configured to output a digitized, over sampled and averaged (DOSA) video signal. The PCSP means is configured to process the DOSA video signal, and configured to output the processed DOSA video signal to an output network interface. The PCSP means is also configured to generate a control signal to control an over sampling rate of the (DOSA) means.

BRIEF DESCRIPTION OF DRAWINGS

The accompanying drawings, which are incorporated in and form a part of this specification, illustrate embodiments of the technology and, together with the description, serve to explain the principles below:

FIG. 6A shows the sensor signal level drift in output signal due to thermal changes in CCD before detection.

FIG. 6B illustrates the start of X-ray detection process showing areas of low density tissue and high density tissue.

FIG. 6C shows how the X-Ray detector detects only signals that exceed the threshold level.

DETAILED DESCRIPTION

Reference now be made in detail to the embodiments of the technology, examples of which are illustrated in the accompanying drawings. While the present technology will be described in conjunction with the various embodiments, it will be understood that they are not intended to limit the present technology to these embodiments. On the contrary, the present technology is intended to cover alternatives, modifications and equivalents, which may be included within the spirit and scope of the various embodiments as defined by the appended claims.

Furthermore, in the following detailed description, numerous specific-details are set forth in order to provide a thorough understanding of the presented embodiments. However, it will be obvious to one of ordinary skill in the art that the presented embodiments may be practiced without these specific details. In other instances, well known methods, procedures, components, and circuits have not been described in detail as not to unnecessarily obscure aspects of the presented embodiments.

Figure 1:
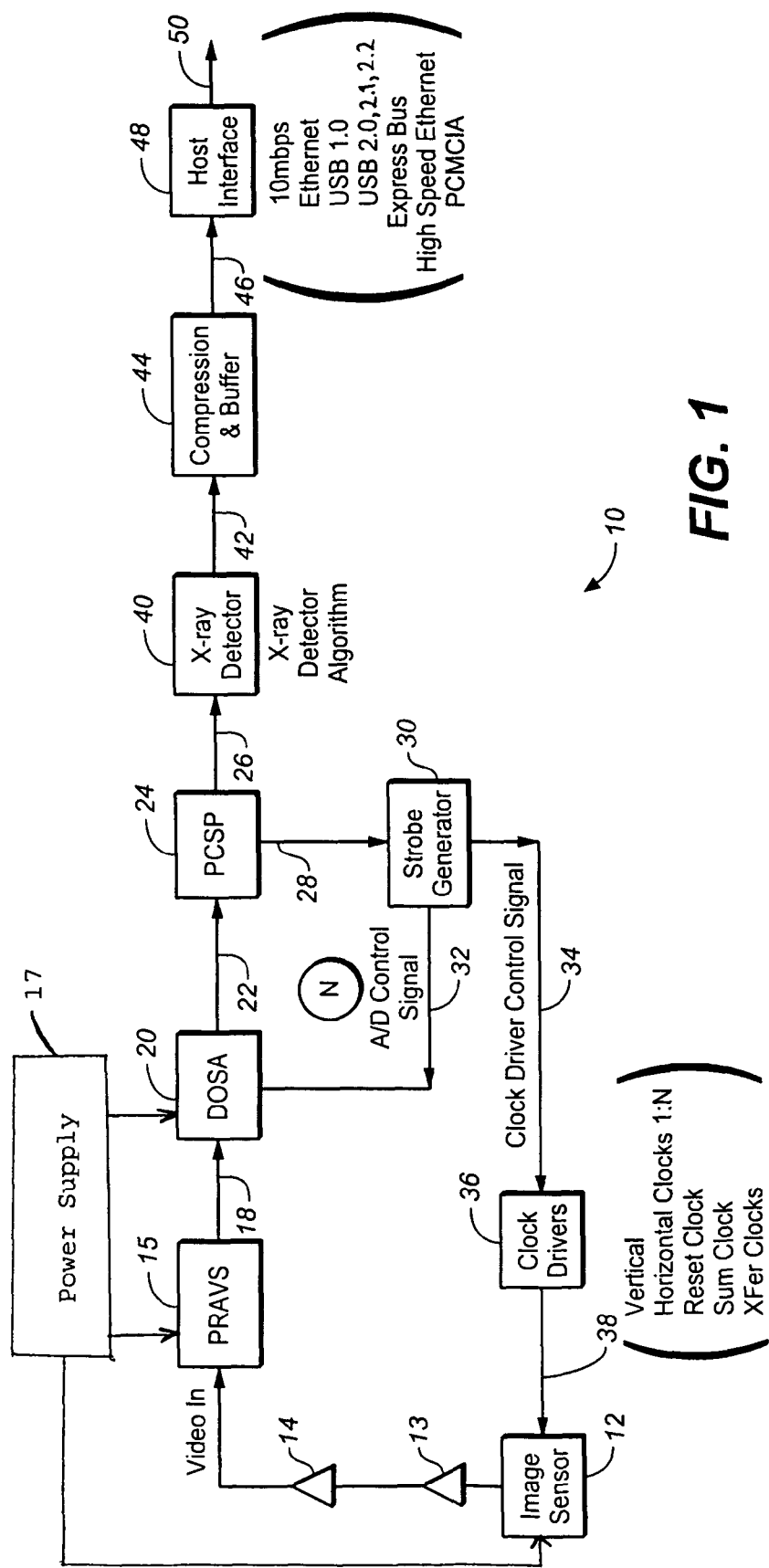
FIG. 1 depicts an implementation of the digital dental image apparatus.

FIG. 1 is a block diagram of the digital dental image apparatus 10 of the present technology that comprises an intra-oral image sensor 12 configured to output a raw analog video signal 14.

The intra-oral image sensor 12 further comprises an X-ray sensitive charge-coupled device (CCD) sensor.

Let us address the background of X-ray imaging. The photographic film is the most widely used detection medium in X-ray imaging applications. It has been used since the discovery of X-rays at the end of the last century. But the principal disadvantage of the X-ray film is its low sensitivity due to the poor absorption. Only about 1% of the incoming radiation is absorbed in the film. In addition, the film needs to be chemical developed before it can be viewed. Major advantage of course is the fact that the film area can be large. This is necessary in medicine, where large organs or objects need to be imaged.

The prospects of digital X-ray imaging systems compared to the photographic film are the higher sensitivity due to an increased absorption and the avoidance of time and material consuming chemical processing. The image is immediately available on the monitor which allows a real-time operation. Also the possibility to apply software image processing tools supports the user to analyze the image. For example, the image can be colored to identify interesting areas more easily.

The digital X-ray imaging systems have already been introduced on the market. The most common sensor concept is the silicon based CCD (charge coupled device). Other detector materials than silicon, such as gallium arsenide, cadmium telluride and cadmium zinc telluride, are now under extensive investigation for array applications. The advantage using these materials is a higher absorption coefficient resulting in a higher sensitivity compared to silicon devices. The higher performance may be used for obtaining images with higher signal-to-noise (SNR) ratio. Alternatively, it may be used for reducing the radiation dose.

Detector arrays for digital X-ray imaging systems may be either of linear or area array type. The former consists of one or a few rows of detector pixels and requires that the object of interest utilized should be scanned. Area arrays are two-dimensional filled with rows and columns of pixels. They require no scanning procedure. For example, for luggage inspection linear detectors are often used since one scanning direction is handled by the moving transportation band.

In contrast to the ultraviolet and the infrared wavelength range, focusing optics is not available for X-rays (or it is very expensive or cumbersome to use). Instead, a shadow image is taken, where the image necessarily is larger than the object to image. When real-time imaging is needed, fluorescent screens, sometimes combined with image intensifiers, can be used. Even in this case the quantum efficiency is low and large X-ray doses have to be utilized, which may be hazardous to the patient.

The CCD was developed as an imager in the early 1970s. Twenty-five years of development has allowed the now mature CCD to be used in a wide variety of high performance scientific, industrial, and military applications. Just as the film in a conventional camera records an image when light strikes it, the CCD records the image electronically.

Typically, a CCD is an array of closely spaced Metal Insulator Capacitors (MIC) separated by channel stops (implanted potential barriers). CCD sensors should perform 4 tasks to generate an image: (1) Generate Charge (by using Photoelectric Effect); (2) Collect Charge (pixels) by using an array of electrodes (called gates); (3) Transfer Charge by applying a differential voltage across gates; signal electrons move down vertical registers (columns) to horizontal register; each line is serially read out by an on-chip amplifier; and (4) Detect Charge, whereas individual charge packets are converted to an output voltage and then digitally encoded.

CCDs consist of thousands or even millions of cells (the largest commercial CCD manufactured contains 9000×7000 elements—roughly 63 million imaging elements), each of which is light-sensitive and capable of producing varying amounts of charge in response to the amount of light they receive. Using a specialized VLSI (Very Large-Scale Integrated circuit) process, a very closely packed array of polysilicon electrodes is formed on the surface of the CCD imaging chip. Conceptually, a CCD is a two-dimensional array of MOS capacitors that collect and transfer photon-generated charge. The difference between a CCD and the other technologies is that the charge from the CCD should be transferred down the parallel column and across the horizontal serial shift register to the amplifier before it can be read out of the array. After charge is collected in each pixel site, the charge is clocked down each column (kept intact by electronic fields induced by applied clock voltages), and into the serial shift register in a method that is often referred to as a "bucket brigade". When the charge reaches the serial shift register, it is transferred perpendicularly along another shift register to one or multiple amplifiers.

To achieve this process, the array of electrodes is clocked (timed) by an off-chip source (timer). It is technically feasible, but not optimal, to use the CCD process to integrate other camera functions, like the clocks, drivers, timing, logic, and signal processing into a single chip. Therefore, these functions are normally implemented in secondary chips. For this reason, most CCD cameras comprise several chips, often three or more. Apart from the need to integrate the other camera electronics in a separate chip, the clock amplitude and shape are critical to successful operation. Generating correctly sized and shaped clock signals normally requires a specialized clock driver chip, and this leads to two major disadvantages: 1) multiple, non-standard supply voltages, and 2) high power consumption. It is not uncommon for CCDs to require five or six different power supplies at critical and obscure values. If a simple single voltage source (such as batteries) is used, then several regulators will be employed internally to generate these supply requirements.

CCD production processes are generally captive to the major manufacturers, but have matured to provide excellent image quality with low noise. The advantage of area array sensors is that they can capture an image all at once, in a single exposure, while maintaining a 100 percent fill factor. Basically, all frame transfer area arrays are built with MOS capacitors that serve as sensing elements, as well as comprise the parallel and serial shift registers. Light is integrated in the photo sites of the imaging region. After a period of integration, i.e. 1/60 of a second for video applications, the charge is quickly transferred down the shift register and into the CCD's storage region, which is covered with an opaque metal layer that blocks the charge from incident light. After all of the charge has been transferred from the active region to the storage region, another integration period can begin. During the integration of the subsequent frame, the charge from the first image is transferred in a parallel-serial fashion to the output amplifier.

One of the critical parameters of the frame transfer CCD is the speed at which the charge can be transferred from the active region (where the charge is integrated) to the storage region. If not shuttered, incident light from the scene is imaged on the CCD while the charge is transferred. Bright spots in the image tend to add unwanted charge to the image as it is transferred through the field-of-view. This undesired characteristic is often referred to as "smear". Values less than 1 percent are desirable.

Like the frame transfer CCD, split frame transfer CCDs use storage regions to store the previous frame's charge, while the next frame is being integrated. However, unlike the frame transfer CCD, the split frame transfer architecture uses storage regions on the top and the bottom of the imager. Half of the image is transferred up into the top storage region and half is transferred down into the other storage region. The advantage of this approach is that the "smear" (the time it takes to transfer the charge from the image into the storage region) is reduced by a factor of two. The disadvantage is that two serial shift registers are required and at least two amplifiers.

Because a full frame CCD imager does not have a storage region, it is half the size of frame transfer type CCDs. With half of the silicon area, the price is proportionally less than frame transfer designs. The disadvantage is that because there is not storage region, the entire image should be read out of the array before the next image can be acquired. This limits the frame rate of full frame cameras.

Like the frame transfer CCD, the two-dimensional interline transfer imager can be conceptually described as an area array with several linear imagers alongside each other. In the interline CCD case, the light sensitive pixels are located near the shielded CCD transport register.

After the charge is integrated in the light sensitive region, the voltage potential of the transfer gate, which forms a barrier between the light sensitive region and the storage region, is raised and the charge from each pixel along the column is transferred into the adjacent storage pixel. The transfer gate is then lowered and the next integration period can commence.

For the interline transfer device to function, it requires that at least half of the imager be covered with an opaque storage region—reducing the effective fill factor. This results in much lower quantum efficiency.

CID imagers have pixels constructed of the same basic structure as CCD imagers—MOS capacitor integrating sites. The difference is how the collected photon generated charge is read. In a CID, each addressable X-Y photo site contains two coupled MOS charge storage areas (photo gates). Simultaneous selection of one or multiple rows and columns defines the coordinates of the pixel to be read out. Driving one photo-gate transfers charge to a second neighboring photo-gate within the same pixel. The charge is then read out. In most implementations, a single amplifier is located per row or per column. Therefore, the charge remains intact to allow further integration or adaptive exposure control. The photo site sampling occurs by a row being selected and making the connection to the readout amplifier. Then, a column is biased to transfer the collected charge from the column to the row at each pixel site. The collected charge at each pixel site remains at the pixel site during the read operation. Only the pixel with its row connected to the output amplifier is read. The column can be re-biased to return the charge into the column for any other pixel in the row to be read or any other row if selected to the output amplifier.

Benefits of the CID structure are random access, front-side sensitive, non-blooming, radiation hard, non-destructive read, and adaptive exposure control. The disadvantage of CID imagers compared to CCD imagers is noise, due to the readout method just described. The charge collected at the pixel site is divided by the buss capacitance of the row, and the buss resistance introduces noise. For this reason, CIDs have not been widely used for most applications.

Referring still to FIG. 1, the present technology utilizes the intra-oral image sensor 12 further comprises an active pixel sensor (APS) array.

Active pixel sensors (APS) are often fabricated using Complimentary Metal Oxide Silicon (CMOS) processing technology (hence the name) to integrate an amplifier at each pixel's site—thereby eliminating the buss capacitance and buss resistance problems of a CID. Whereas previously the transistors used for manufacturing CMOS APS sensors covered the whole integrating area, the transistor sizes are now small enough that they only cover approximately 75 percent of the imager area—allowing for light to get through a portion of the pixels. It was not until sub-micron photolithography became available that APS imagers became useful. As the readout circuitry of the APS consumes a large portion of the pixel cell, more improvements will be required to increase the sensitivity of the device so that it can be used for high performance applications. Micro lenses, which are used to focus light away from the circuitry and onto the sensitive portion of the photo site, like most optical components are designed for specific incident light angles and spectral wavelength. Generally, micro lenses are not useful for fast, high performance optical systems.

At the present state of the art, active pixel sensors are best suited for linear arrays until the deep sub-micron CMOS processes become readily available. Linear arrays eliminate the problem of the amplifier taking up active imaging area by placing the amplifier adjacent to the pixel sites.

CMOS imagers sense light in the same way as CCDs—both technologies convert incident light (photons) into electronic charge (electrons) by the same photo-conversion process. Color sensors can be made in the same way with both technologies; normally by coating each individual pixel with a filter color (e.g. red, green, and blue)—but beyond that point, everything is different. The charge packets are not transferred; they are instead detected as early as possible by charge sensing amplifiers, which are made from CMOS transistors. CMOS imaging technologies can support two flavors of photo element: the photo gate and the photodiode. Generally, photodiode sensors are more sensitive, especially to blue light, which can be important in making color cameras. In some CMOS sensors, amplifiers are implemented at the top of each column of pixels—the pixels themselves contain just one transistor, which is used as a charge gate, switching the contents of the pixel to the charge amplifiers. These "passive pixel" CMOS sensors operate like analog DRAMs. In other CMOS sensors, amplifiers are implemented in each and every pixel—these are called "active pixel" CMOS sensors. Active pixel CMOS sensors usually contain at least three transistors per pixel. Normally, the active pixel form has lower noise but poorer packing density than passive pixel CMOS.

Because CMOS active pixel sensors can be manufactured on conventional CMOS production lines; they offer the potential for significantly lower cost and also offer the capability to be integrated with other functions such as timing logic and analog-to-digital conversion. The promised benefits of the technology include: lower power, random readout, and ADC and timing fabricated on chip (camera on a chip). The CMOS process allows the integration of an amplifier at each site. More importantly, active pixel sensors, in theory, are able to utilize the high level of CMOS integration that can make an imaging system or camera on a chip not just an imager.

However, because of the inherently higher noise of the APS sensors (due to the readout structure), the lower quantum efficiency (due to the lower fill factor), and the compromises in semiconductor manufacturing made to incorporate multiple features on a single die, at the present state of the art APS sensors have only been used for toys and low end consumer electronics.

The problem with multi-functional CMOS sensors, combining large pixel densities with other functions, is similar to the lessons learned long ago by the rest of the semiconductor market—systems-on-a-chip offer several shortcomings, including budget busting cost of the ultra-large die and limited access to embeddability of leading edge intellectual property. Hybrid approaches and multi-chip modules are popular for this very reason.

Different functions of the image sensor technology require different semiconductor manufacturing processes. Moreover, although CMOS is generally used to describe a technology family, there are a wide variety of semiconductor processes used to manufacture CMOS devices. The process for a DRAM memory device is dramatically different than an analog-to-digital converter (ADC) and an amplifier. Each company tends to focus on optimizing a process to optimize performance for a very specific market niche. This prohibits optimal multi-function CMOS APS device. Performance is optimized using a hybrid approach as opposed to integration on a single chip.

In an embodiment, the digital dental image apparatus 10 also includes a low noise power supply system 17 that can be implemented by using a rechargeable battery, or a large capacitor including a charger. The low noise power supply system 17 improves the CCD/CMOS sensor performance. Indeed, the battery 17 having a sufficiently high voltage is substantially a low dropout (LDO) voltage regulator. LDO voltage supply system has a low noise as opposed to a regular fixed (wall) power source, which results in a better signal-to-noise ratio (SNR) of the CCD/CMOS sensor. In addition, in mobile or wireless applications, use of a battery or large capacitor eliminates the need for a fixed (wall) power source.

Figure 2:
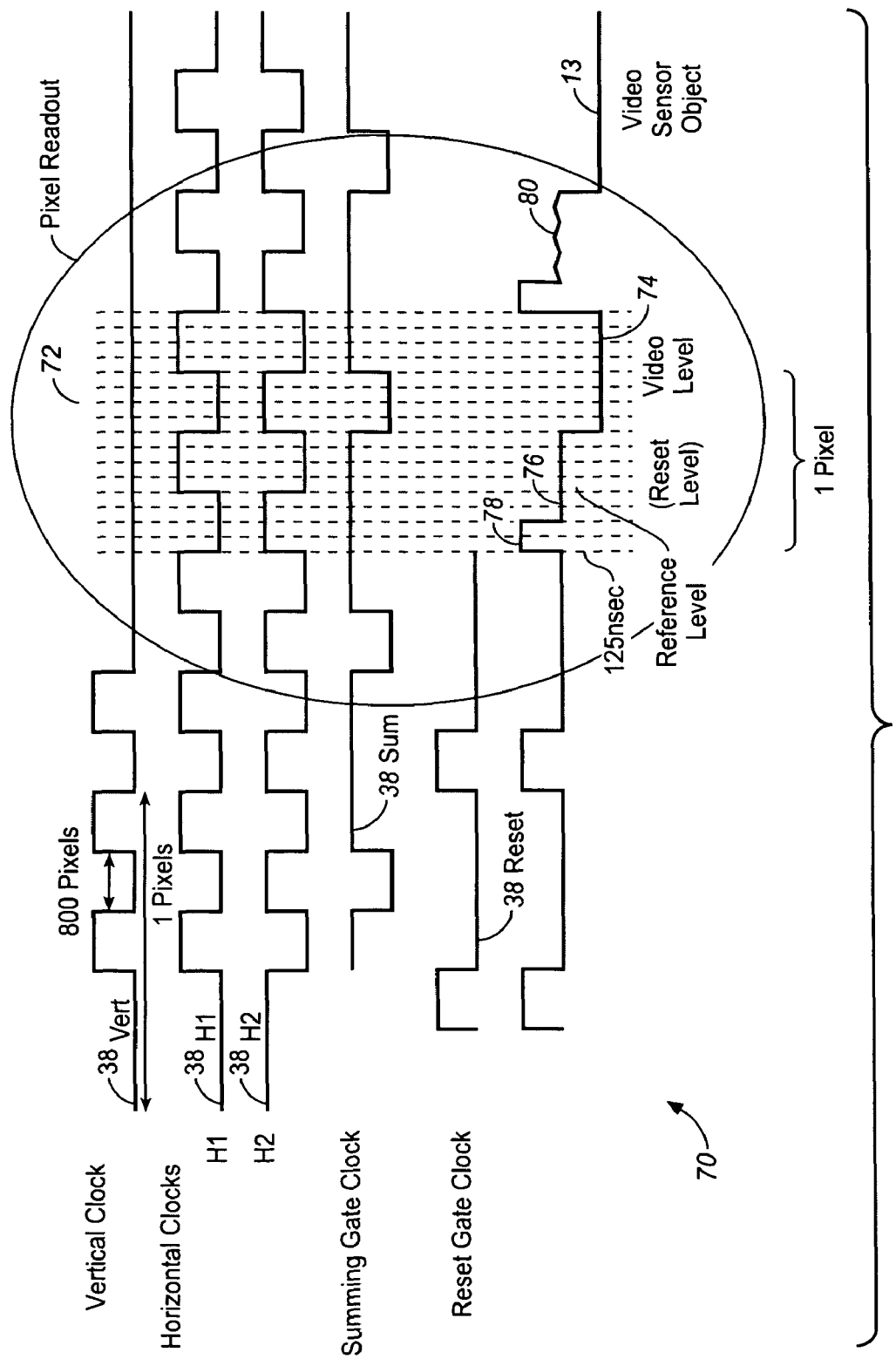
FIG. 2 illustrates a plurality of clock signals of block diagram of FIG. 1 including: a vertical clock signal, a first horizontal clock signal, a second horizontal clock signal, a summing gate clock signal, a reset clock signal, and an analog sensor video output readout signal, which is also an input video signal block diagram of FIG. 1.

FIG. 2 illustrates a plurality of clock signals 38 of FIG. 1 {a vertical clock $38_{Vertical}$; a first horizontal clock signal $38_{H1}$; a second horizontal clock signal $38_{H2}$; a summing gate clock signal $38_{sum}$; and a reset clock signal $38_{reset}$}; and an analog sensor video output signal 13, which is also an input video signal 14 (of FIG. 1) for the purposes of the present technology. As shown in FIG. 2, vertical clocks $38_{Vertical}$ are typically 800 pixels apart, whereas within one pixel 72 there are several horizontal clock signals $38_{H1}$ and $38_{H2}$.

Figure 2A:
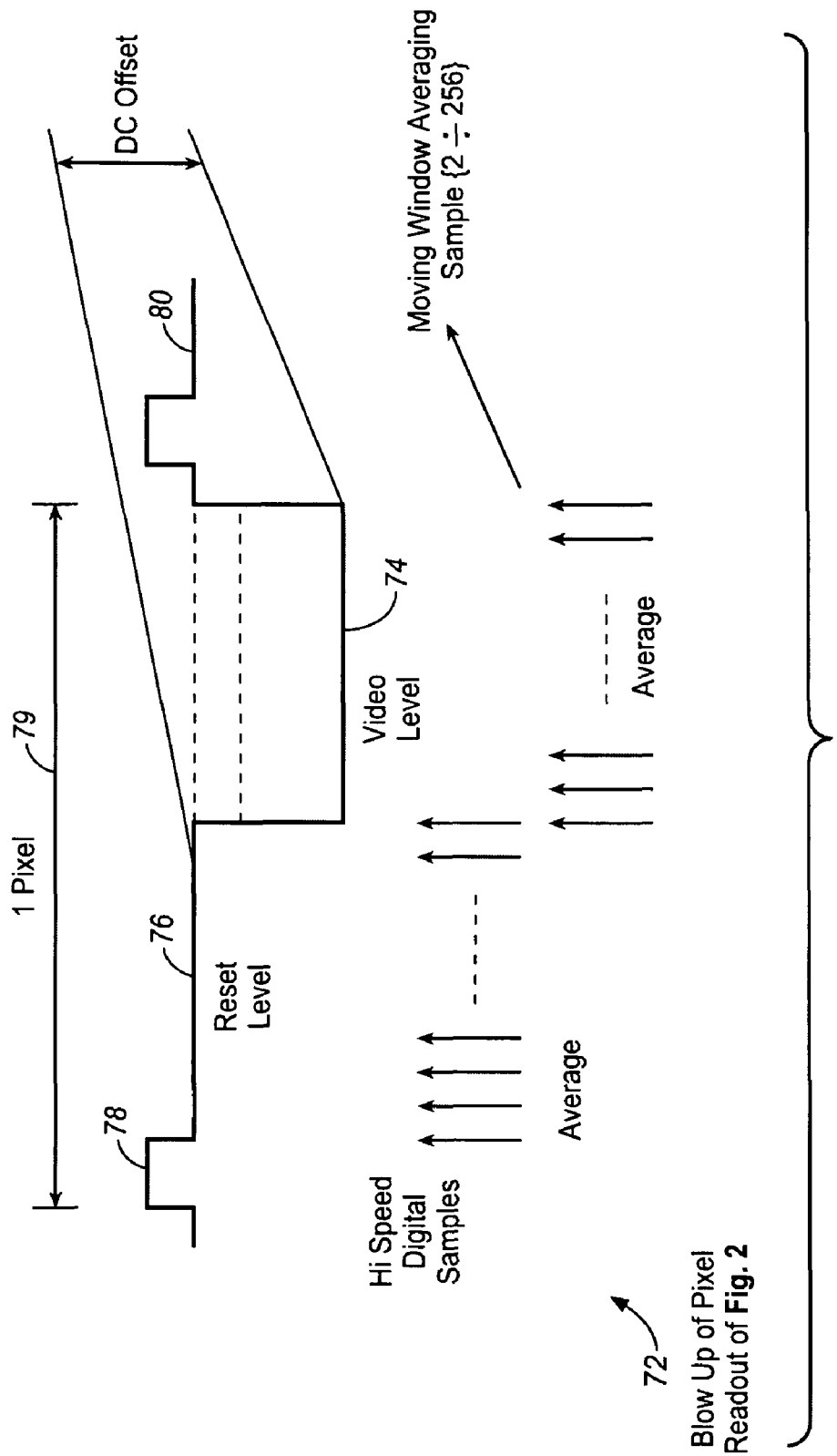
FIG. 2A shows a blow up of the pixel readout of block diagram of FIG. 2.

In an embodiment, FIG. 2A shows a blow up of the pixel readout 72 of FIG. 2 in more detail. The reset (reference) level 76 and the video level 74 are sampled at high speed by DOSA block 20 (of FIG. 1) to obtain a moving averaging of reference level 76 and of video level 74. So, one can measure the analog D/C offset by calibrating CCD sensor 12 (of FIG. 1) before actually taking X-ray.

Figure 3A:
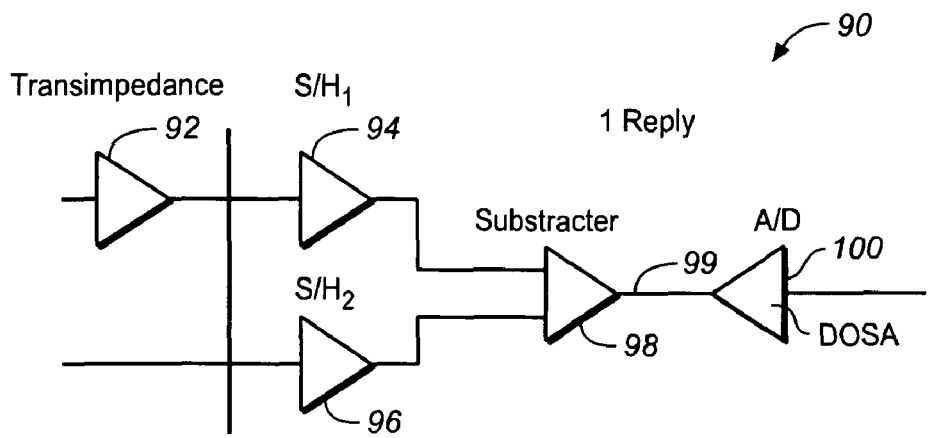
FIG. 3A depicts the PRAVS block further comprising a trans impedance amplifier block configured to level shift an amplitude of the raw analog video signal to an optimum voltage level, and a dual sample & hold (S/H) block including an analog subtractor block.

With reference to FIG. 3A, in an exemplary embodiment, the PRAVS block 90 (15 of FIG. 1) further comprises a trans impedance amplifier block 92 configured to level shift an amplitude of the raw analog video signal to an optimum voltage level, a dual sample & hold (S/H) blocks 94 and 96, and an analog subtractor block 98.

Figure 3B:
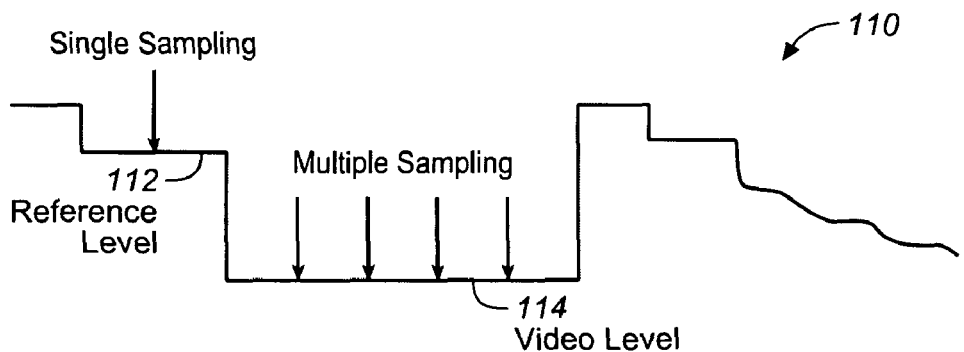
FIG. 3B illustrates the signals associated with the functioning of the PRAVS block of FIG. 3A.
Figure 3C:
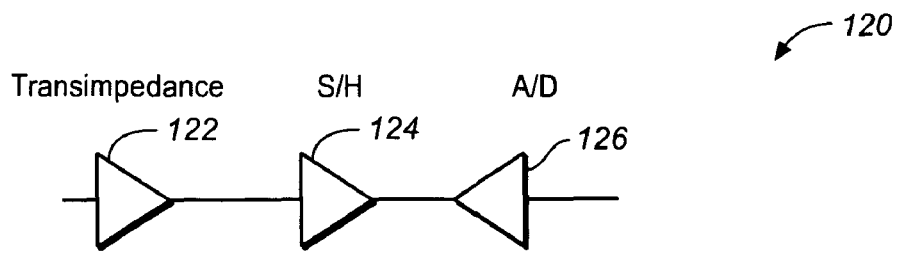
FIG. 3C depicts the PRAVS block further comprising a trans impedance amplifier block configured to level shift an amplitude of the raw analog video signal to an optimum voltage level, and a single sample & hold (S/H) block.
Figure 3D:
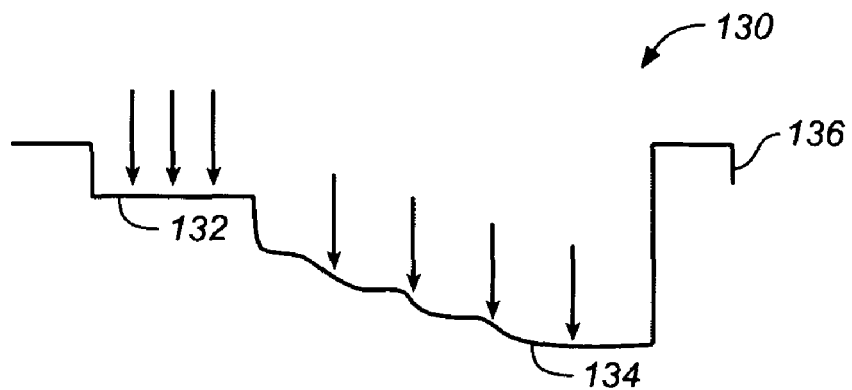
FIG. 3D illustrates the signals associated with the functioning of the PRAVS block of FIG. 3C.
Figure 3E:
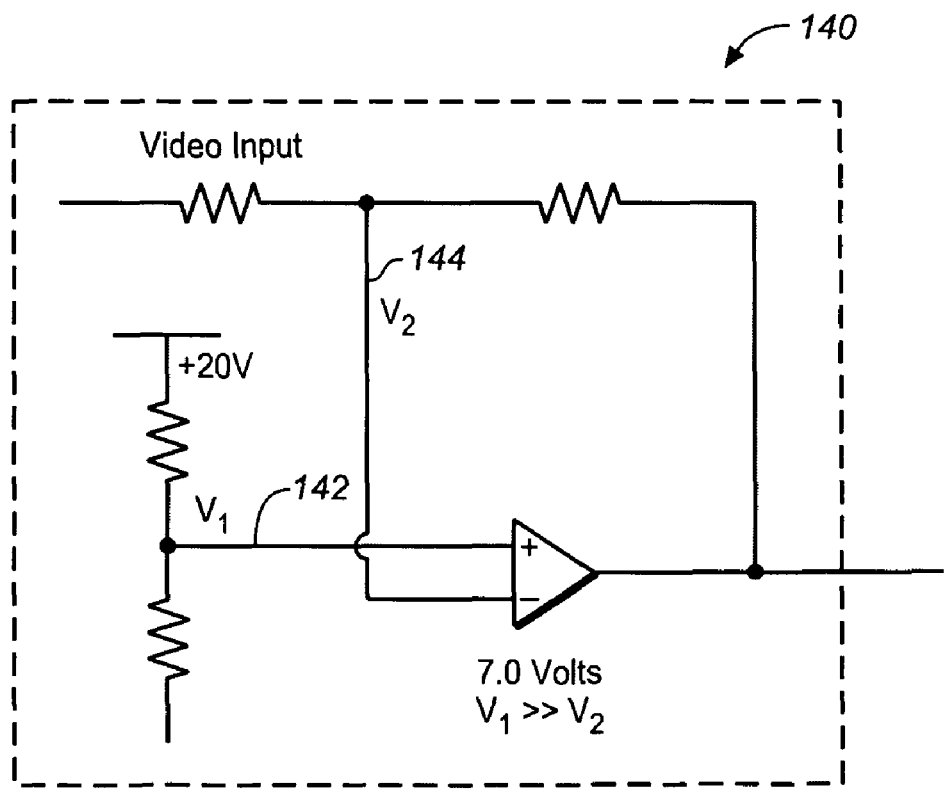
FIG. 3E shows the trans impedance amplifier block in more detail.

With the further reference to FIG. 3E, in another exemplary embodiment, the trans impedance amplifier block 92 is shown in more detail. The trans impedance amplifier block 92 shifts level via difference in voltages (V1–V2) and minimizes the output impedance (it is approximately zero ohms). Lower impedance provides noise immunity.

The first $S/H_1$ block 94 is configured to output a video reference signal, whereas the second $S/H_2$ block 96 is configured to output a raw video signal, and the analog subtractor block 98 configured to subtract the reference video signal from the raw video signal to obtain an adjusted video voltage level 99 (18 of FIG. 1). The reference and actual video levels may be actually very close in value when the X-ray has yet to occur, or in the very beginning. It is essential that both S/H circuits are configured so that the initial X-ray exposure is detected even it is an initial insufficient burst.

With the further reference to FIG. 3B, in another exemplary embodiment, it is shown how the reference level 112 and the video level 114 are sampled for further processing. More specifically, there is a single sampling of the reference level 112, and the multiple sampling of the video level 114.

Sample and hold circuits (S/H) are used herein for sampling values of continuous time-varying amplitude signal at discrete time intervals. The sample and hold circuits are employed herein as part of an analog-to-digital signal conversion process, such that the amplitude values of analog input signals are sampled at timed intervals and converted into digital values to provide a digital output representation of the time varying amplitude signal. Without proper detection, a series of small X-ray bursts from the X-ray detector prior to the main burst will result in a sort of double exposure since the CCD clock was not stopped. Without stopping the CCD clocks at the first detection of X-ray energy, a portion of the spatial location will be saved in multiple CCD locations.

The sample and hold switches are typically implemented employing Metal-Oxide Semiconductor Field Effect Transistors (MOSFETs). In the conventional sample and hold circuits, the signals that control the switching of the sample and hold switches or MOS transistors are simple digital signals. The "ON" resistance of the MOSFET is the resistance between the source region and the drain region when the transistor is "ON" or conducting, which is a function of the gate to source voltage and the source to back gate voltage. Therefore, the resistance of the input sampling switch varies with the input signal level. This causes the voltage across the capacitor C at the sampling instant to change with the amplitude of the input signal due to the non-linearity of the sampling switches.

With the further reference to FIG. 3C, in an exemplary embodiment, the PRAVS means 120 further comprises: a trans impedance amplifier block 122 configured to level shift an amplitude of the raw analog video signal to an optimum voltage level range; and a single sample & hold (S/H) circuit 124. In this embodiment of the present technology, a first sample to the S/H block is strobed during a video reference level of a pixel, whereas a second sample to the S/H block is strobed during a raw video level of the pixel. Each analog sample is digitally converted in block 126, whereas two digital samples are digitally subtracted to obtain an adjusted video level.

With the further reference to FIG. 3D, in an exemplary embodiment, the reference level of the pixel 132 and the raw video level of the pixel 134 are multiply sampled in the further processing.

Referring still to FIG. 1, the digital dental image apparatus 10 further comprises a digitizing, over sampling, and averaging (DOSA) block 20 configured to digitize, over sample, and average the optimized analog video signal 18. The DOSA block 20 is configured to output a digitized, over sampled and averaged (DOSA) video signal 22. The DOSA block 20 further comprises a high rate A/D converter configured to output a digitized, over sampled and averaged (DOSA) video signal 22 under control of the A/D control signal 32 generated by the Strobe Generator 30. The Strobe Generator 30 can be implemented by using a high current MOSFET.

There are certain advantages of over sampling. Indeed, the over sampling results in increase in the signal-to-noise ratio (SNR) since the noise is uncorrelated and the signal is biased. The increase in SNR is 10×Log 10×(Number of Samples). For example, if the 10 samples of the reference and 10 samples of the signal are obtained, the increase in the SNR is 10 dB. {10×Log 10=10×1=10.}

Typically, the over sampling is performed by an integer N factor ranging between 2 and 256. For example, to double the SNR from 3 to 6 dB the over sampling by factor 2 can be used. It will result in increase of the probability of detection and decrease the probability of false detection.

By performing the pixel subtractions digitally, all but the initial instrumentation amplifier can be eliminated. Negative pixels levels can be even accommodated. Further more, non-linearities in the A/D step sizes, (quantization non-linearities) can be attenuated by noise shaping (i.e., adding some additional noise at given frequencies to attenuate this effect). Additional calibration, such as the dark current mask and blemish removal can be performed in the processor before transmission to host computer via Ethernet. Further reference levels checks may indicate impulse noise. Please, see the discussion below.

Referring still to FIG. 1, the digital dental image apparatus 10 further comprises a programmable control and signal processing (PCSP) block 24 configured to process the DOSA video signal 22, and configured to output the processed DOSA video signal 26. In an exemplary embodiment, the PCSP block 24 is configured to generate a control signal 28 to control an over sampling rate of the (DOSA) block 20. The programmable control and signal processing (PCSP) block 24 can be implemented by using a DSP microprocessor, a FPGA, or an ASIC.

In any operation where the bit-depth of the quantization is reduced (e.g., when a 24-bit file is re-saved as a 16-bit file), then it is generally recommended to apply dither to reduce the non-linear amplitude distortion caused by re-quantization. In essence, the application of dither amounts to adding low-level random noise to the signal. By selecting the noise amplitude comparable to the quantization step size, the effect of the dither is to linearize the input-output characteristics of the quantizer, thereby increasing the effective resolution. The perceived additional noise can be minimized by use of an appropriately-designed noise-shaping filter incorporated with the dithering process.

In an embodiment of the present technology, the PCSP block further comprises a noise shaper block (not shown) further comprising a noise shaper algorithm configured to attenuate non-linearities in the A/D quantization steps, and configured to minimize Integrated Non-Linearity (INL) & Differential Non-Linearity (DNL) of the DOSA video signal. With a noise shaper block, a lower performance A/D (that is, a cheaper A/D) can be used. The noise shaper block can be implemented by using a DSP microprocessor, a FPGA, or an ASIC.

Figure 4A:
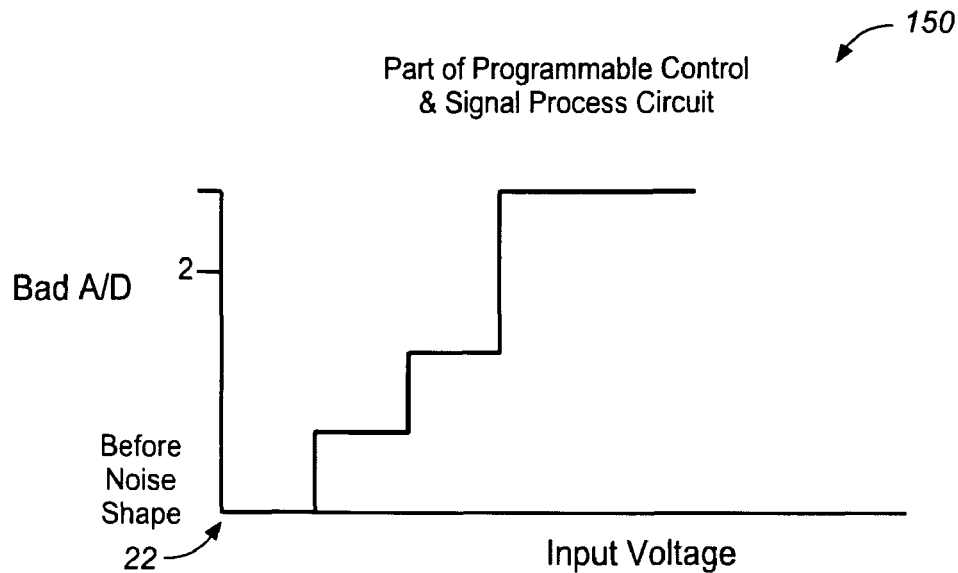
FIG. 4A is a diagram illustrating a digital signal outputted by the block DOSA before noise shaping takes place.

In an embodiment of the present technology, as shown in FIG. 4A, diagram 150 illustrates a digital signal 22 (of FIG. 1) outputted by the block DOSA 20 (of FIG. 1) before noise shaping takes place.

Figure 4B:
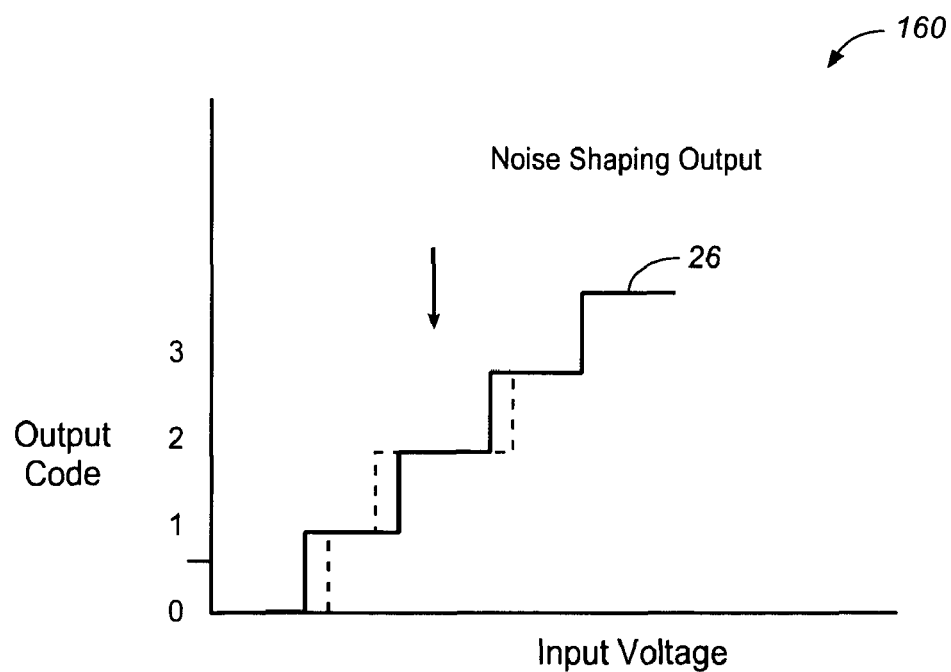
FIG. 4B illustrates the output code from the PCSP block after the noise shaping is performed, whereas the output code still has some quantization errors.

In an embodiment of the present technology, with the reference to FIG. 4B, the noise shaping results in the output code 26 (of FIG. 1) from the PCSP block 24 (of FIG. 1). However, output code 26 still has some quantization errors.

Figure 4C:
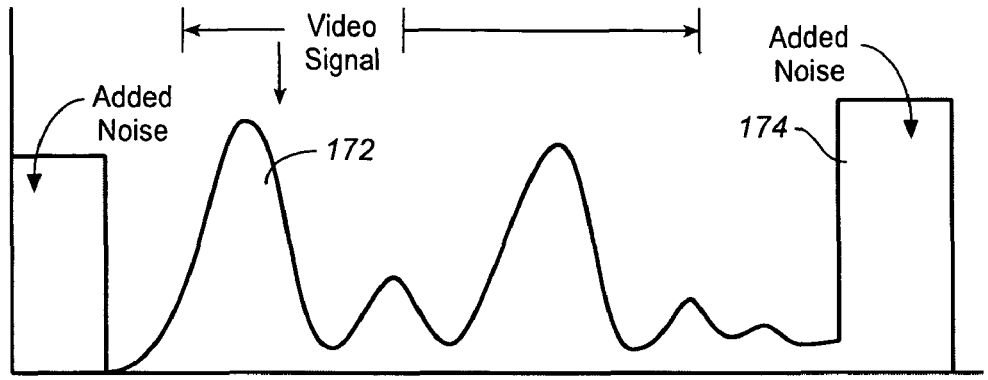
FIG. 4C shows how to dither digital steps and how to minimize the quantization errors in the processed DOSA video signal by using non-Gaussian digital noise.

In an embodiment of the present technology, the noise shaper block further comprises a non-Gaussian digital noise block configured to add a non-Gaussian digital noise 174 to dither digital steps and to minimize the quantization errors in the processed DOSA video signal 172, as shown in the diagram 170 of FIG. 4C. The non-Gaussian digital noise block can be implemented by using a DSP microprocessor, a FPGA, or an ASIC.

Figure 4D:
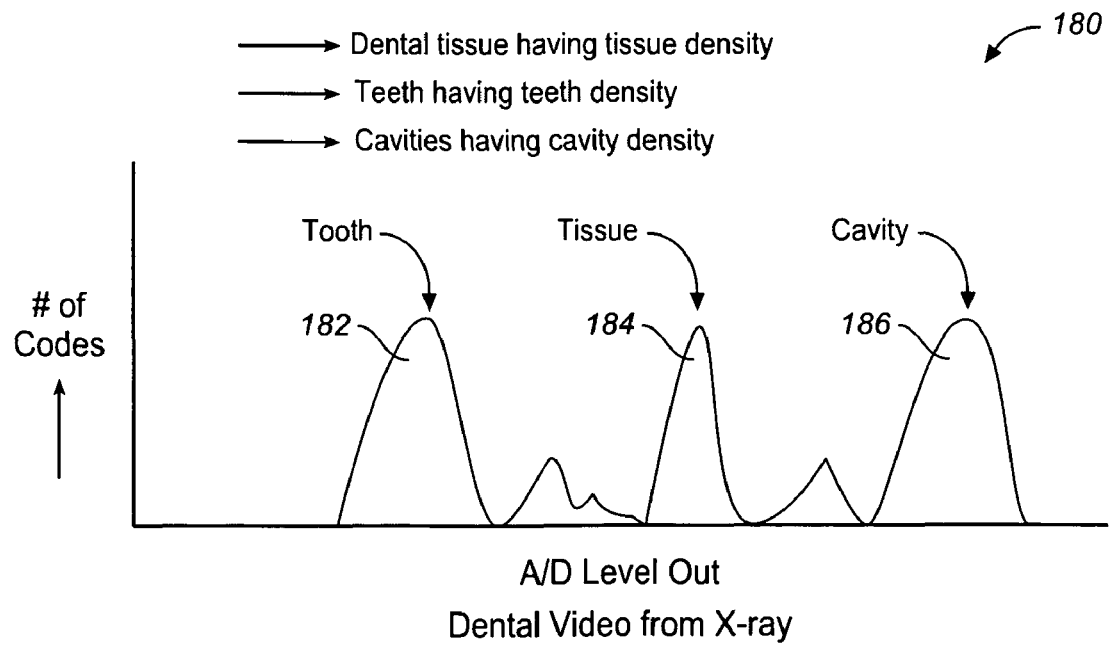
FIG. 4D depicts (number of codes v. A/D level) for tooth-cavity, for tooth itself, and for tooth tissue.

More specifically, with the reference to diagram 180 of FIG. 4D, in imaging, high frequency components are "edges" (186-cavity), whereas the low frequencies are "blurs" or "gradual transitions" (182-tooth), with the intermediate frequencies (tissue 184) in between.

Figure 4E:
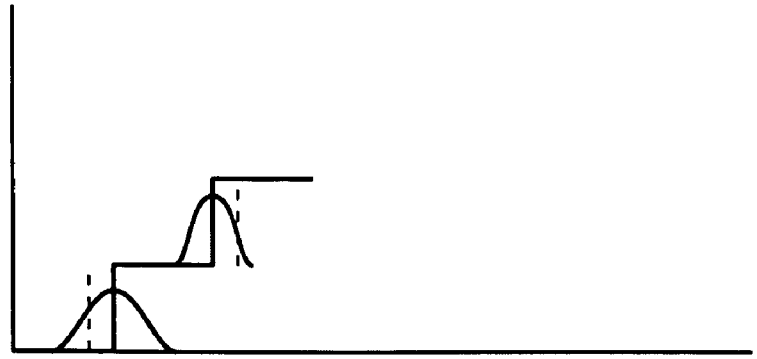
FIG. 4E illustrates the differential non-linearities (DNL) and integrated non-linearities (INL).

With the reference to FIG. 4E, the differential non-linearities (DNL) and integrated non-linearities (INL) in the diagram 190 are illustrated. In a receiver, non-linear steps cause intermodulation. Due to noise shaping there is less quantization error.

Figure 5:
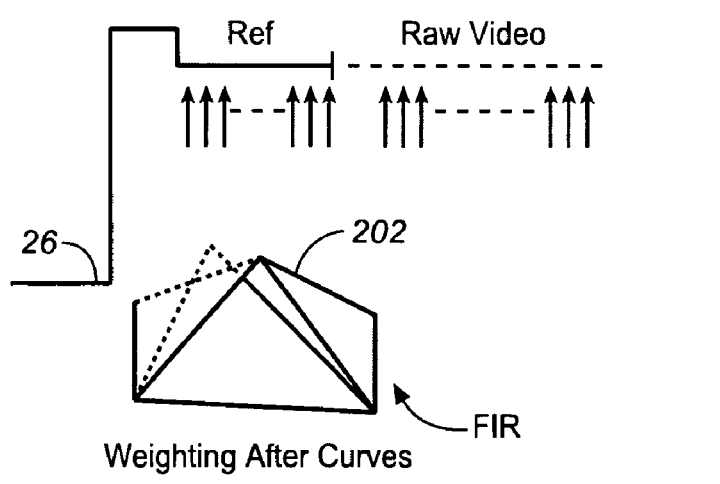
FIG. 5 illustrates the effect of averaging on the video pixel readout performed by the PCSP.

With the reference to FIG. 5, the effect of averaging performed by the PCSP block 24 (of FIG. 1) on the video pixel readout 26 (of FIG. 1) is illustrated. PCSP block can be programmed to perform the required averaging. More specifically, the programmable Finite Impulse Response (FIR) filter can be used to perform the required averaging.

In an exemplary embodiment of the present technology, the programmable control and signal processing (PCSP) block 24 implements the following logic:

(1) Vertical rows are clocked by using a vertical clock signal $38_{vertical}$.

(2) Each row is completely horizontally clocked by using horizontal clock signals $38_{horizontal\_1}$ and $38_{horizontal\_2}$, and video level is determined.

(3) Edges and blemishes are ignored through database of locations on the card that indicates which readout points to ignore.

(4) An impulse reduction filter is used that compares row to row energy increase and determines if an X-ray occurred. The row filtering is also performed within each row.

(5) If X-ray threshold is exceeded, the clocking of CCD is halted and X-ray integration occurs for 300 msec typically.

(6) Otherwise, clocking and readout continues to eliminate dark current build-up in CCD.

(7) An impulse reduction filter eliminates impulse external noise.

Referring still to FIG. 1, in an embodiment, the digital dental image apparatus 10 further comprises a Strobe generator 30 configured to generate an A/D control signal 32 to control the DOSA block 20. The Strobe generator 30 is controlled by the PCSP block 24 via the control signal 28.

With the reference to FIG. 1, in an embodiment, the digital dental image apparatus 10 further comprises a clock drivers block 36. The clock drivers block 36 is configured to output a plurality of clock signals 38 configured to control the sensor 12. The plurality of clock signals 38 can be selected from the group consisting of: {reset clock signal $38_{reset}$; summing gate clock signal $38_{summing}$; horizontal clock signals $38_{horizontal\_1}$ and $38_{horizontal\_2}$; vertical clock signal $38_{Vertical}$; and a transfer clock signal}. The clock drivers block 36 is controlled by a clock drivers control signal 34 generated by the Strobe generator 30. The clock drivers block 36 can be implemented by using high current MOSFET Drivers.

Referring still to FIG. 1, in an embodiment, the digital dental image apparatus 10 further comprises an X-ray detector 40 configured to perform an X-ray detection to filter out a false detection caused by noise. The X-ray detector block is configured to output a real video signal 42 indicative of a real X-ray detection. X-ray detector 40 can be implemented by using a DSP microprocessor, a FPGA, or an ASIC.

Sensors have variation in level and noise variance. Good sensors have levels variance. Detection of X-ray is deemed to occur when level rises to exceed "maximum" variance. Sensor response can be triggered by noise if threshold is lower than sensors' variation of detectable level. So, one might have a "false start", and, on the other hand, another sensor might miss the start of the detection.

The solution is to introduce the intelligence in the detection process by using the X-ray detector 40 (of FIG. 1). Indeed, FIG. 6A shows the sensor signal level drift 210 in output due to thermal changes in CCD before detection. FIG. 6B illustrates the start of X-ray detection process 220 showing areas of low density tissue and high density tissue. FIG. 6C shows how the X-Ray detector detects only signals 222 (26 of FIG. 1) that exceed the threshold level 224.

Figure 7A:
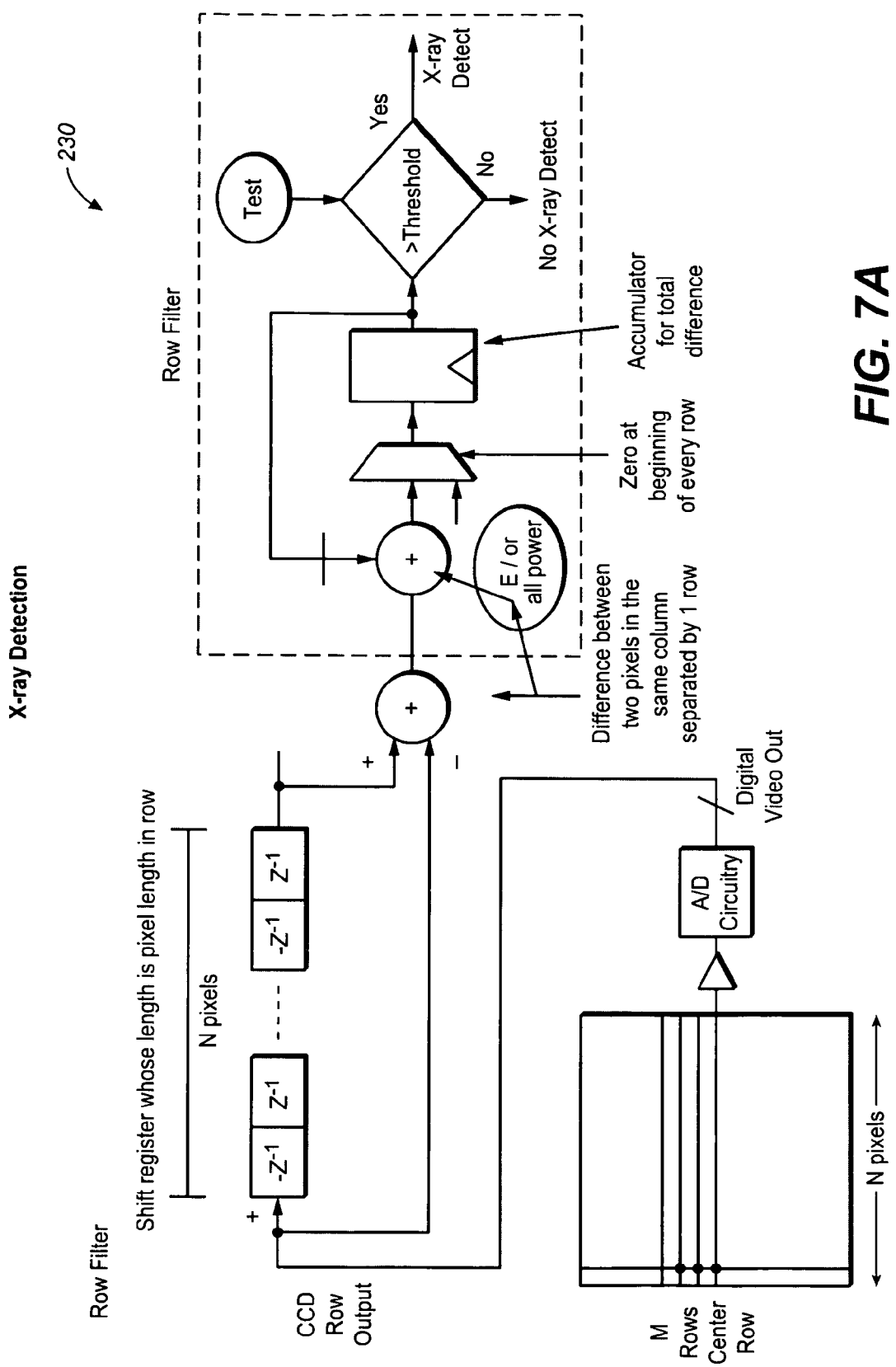
FIG. 7A shows the X-ray detector in more detail.

In an embodiment, FIG. 7A shows the X-ray detector 230 (40 of FIG. 1) in more detail. The X-ray detector 230 implements the following detection algorithm:

(A) pixel adjusted levels are compared row-to-row, i.e, level [n, m]–level [n+1, m] and summed across a row;
(B) if the sum exceeds a threshold, X-ray detection is declared;
(C) in order to suppress impulse noise, the reference level is compared row-to-row and column-to-column, and an adjustment is made to minimize false detection.

The all-digital technique is superior since the level at reference and the level for the video are all being digital through the same analog path. Thus, all biases and gains are common mode.

Figure 7B:
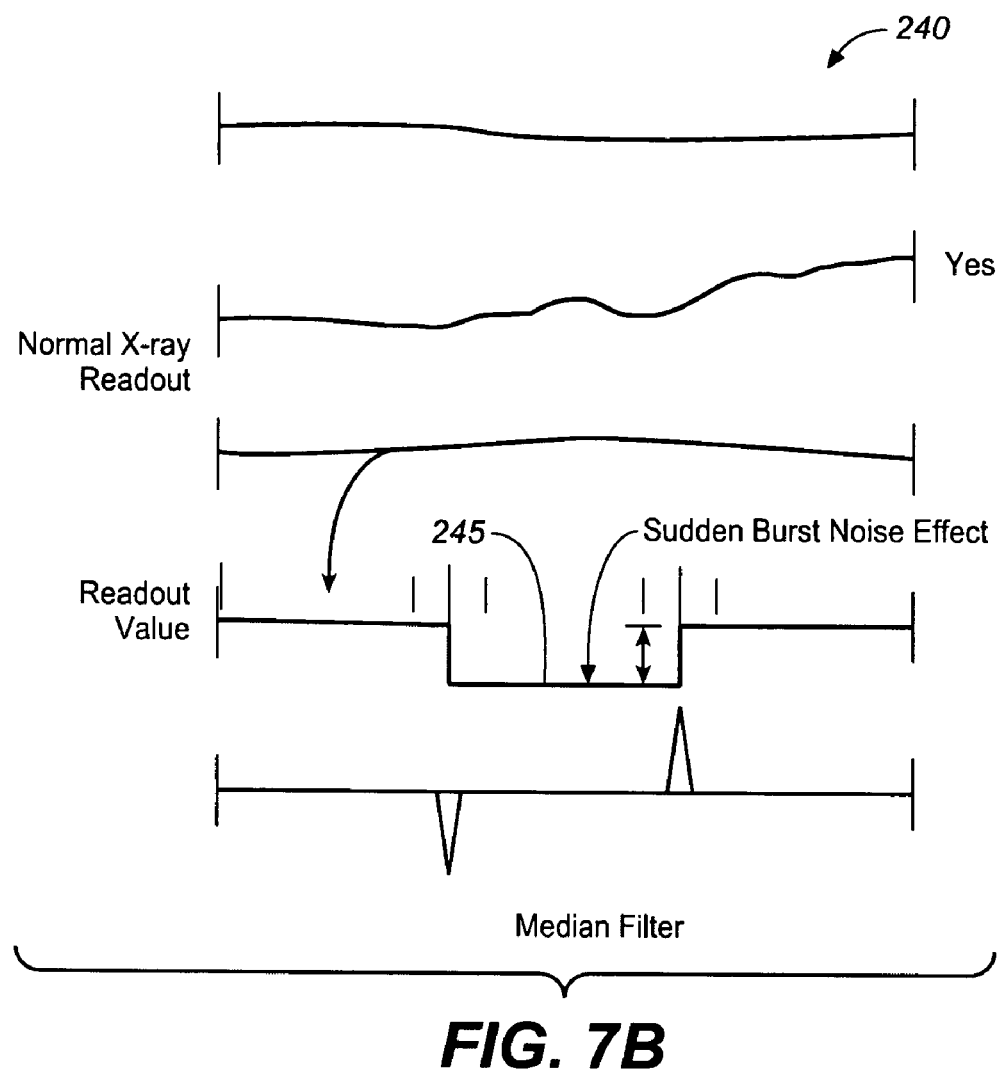
FIG. 7B illustrates the functioning of the median filter that is configured to filter out a sudden burst noise effect.

With the reference to FIG. 7B, the diagram 240 illustrates the detection process, whereas the X-ray detector 230 (of FIG. 7A) further includes the median filter (not shown) that allows one to get rid of sudden burst noise effect 245 (of FIG. 7B) that could be mistakenly interpreted as a real signal.

When performing median filtering, each pixel is determined by the median value of all pixels in a selected neighborhood (mask, template, and window). The median value m of a population (set of pixels in a neighborhood) is that value in which half of the population has smaller values than m, and the other half has larger values than m. This class of filter belongs to the class of edge preserving smoothing filters which are non-linear filters. These filters smooth the data while keeping the small and sharp details.

Thus, a median filter tosses the outlying points from further computation. Trying to detect sudden burst noise effect, one should look at the reference level because the changes at the reference level can be associated only with noise, not with X-ray signal itself. For instance, if one touches the sensor by hand, it can cause the reference level to go up because of sudden burst noise effect, but it would not affect the video level.

Referring still to FIG. 1, in an embodiment, the digital dental image apparatus 10 further comprises compression & buffer block 44 configured to compress, to store, and to output the real processed video signal 46 to the output network interface 48. The compression & buffer block 44 can be implemented by using a DSP microprocessor, a FPGA, or an ASIC.

In an embodiment, the output network interface 48 is selected from the group consisting of: {a low speed output network interface; and a high speed output network interface}. The low speed output network interface is selected from the group consisting of: {10 mbps Ethernet; USB 1.0; USB 2.0; USB 2.1; and USB 2.2}. The high speed output network interface is selected from the group consisting of: {100 mbps Ethernet; Gigabit Ethernet; USB 2.0; USB 2.1; USB 2.2; Express Bus; and PCMCIA}.

In an embodiment, the method of the present technology comprises: (A) obtaining an intra-oral image by using an intra-oral image sensor, whereas the intra-oral image sensor is configured to output a raw analog video signal including the intra-oral image; (B) processing the raw analog video signal for optimum detection by using a block for processing the raw analog video signal (PRAVS), whereas the PRAVS block is configured to output an optimized analog video signal; (C) digitizing, over sampling, and averaging the optimized analog video signal by using a digitizing, over sampling, and averaging (DOSA) block, whereas the DOSA block is configured to output a digitized, over sampled and averaged (DOSA) video signal; and (D) processing the DOSA video signal by using a programmable control and signal processing (PCSP) block, whereas the PCSP block is configured to output the processed DOSA video signal to an output network interface.

In an embodiment, the method of the present technology further comprises the step of generating a control signal configured to control an over sampling rate of the (DOSA) block. More specifically, the method of the present technology further comprises the step (E) of generating an A/D control signal to control the DOSA block by using a Strobe generator under programmable control of the PCSP block.

In an embodiment, the method of the present technology further comprises: the step (F) of controlling the sensor by a plurality of clock signals generated by a clock drivers block. The clock drivers block is controlled by a clock drivers control signal generated by the Strobe generator, whereas the plurality of clock signals are selected from the group consisting of: {a reset clock signal; a summing gate clock signal; horizontal clock signals; vertical clock signals; and a transfer clock signal}.

In an embodiment, the method of the present technology further comprises: the step (G) of performing X-ray detection to filter out a false detection caused by noise by using an X-ray detector block; the step (H) of outputting a real video signal indicative of a real X-ray detection by using the X-ray detector block; the step (I) of compressing, storing, and outputting the real processed video signal to an output network interface by using a compression and buffer block; and the step (K) of transferring a plurality of images to a recipient selected from the group consisting of: {dentists; physicians; insurers; and storage systems} by using an output network interface.

The above discussion has set forth the operation of various exemplary systems and devices, as well as various embodiments pertaining to exemplary methods of operating such systems and devices. In various embodiments, one or more steps of a method of implementation are carried out by a processor under the control of computer-readable and computer-executable instructions. Thus, in some embodiments, these methods are implemented via a computer.

In an embodiment, the computer-readable and computer-executable instructions may reside on computer useable/readable media.

Therefore, one or more operations of various embodiments may be controlled or implemented using computer-executable instructions, such as program modules, being executed by a computer. Generally, program modules include routines, programs, objects, components, data structures, etc., that perform particular tasks or implement particular abstract data types. In addition, the present technology may also be practiced in distributed computing environments where tasks are performed by remote processing devices that are linked through a communications network. In a distributed computing environment, program modules may be located in both local and remote computer-storage media including memory-storage devices.

Although specific steps of exemplary methods of implementation are disclosed herein, these steps are examples of steps that may be performed in accordance with various exemplary embodiments. That is, embodiments disclosed herein are well suited to performing various other steps or variations of the steps recited. Moreover, the steps disclosed herein may be performed in an order different than presented, and not all of the steps are necessarily performed in a particular embodiment.

Although various electronic and software based systems are discussed herein, these systems are merely examples of environments that might be utilized, and are not intended to suggest any limitation as to the scope of use or functionality of the present technology. Neither should such systems be interpreted as having any dependency or relation to any one or combination of components or functions illustrated in the disclosed examples.

Although the subject matter has been described in a language specific to structural features and/or methodological acts, the subject matter defined in the appended claims is not necessarily limited to the specific features or acts described above. Rather, the specific features and acts described above are disclosed as exemplary forms of implementing the claims.

What is claimed is:

1. A digital dental image apparatus comprising:
    an intra-oral image sensor configured to output a raw analog video signal;
    a processing raw analog video signal (PRAVS) means for processing said raw analog video signal for optimum detection; said PRAVS means configured to output an optimized analog video signal;
    a digitizing, over sampling, and averaging (DOSA) means for digitizing, over sampling, and averaging said optimized analog video signal; said DOSA means coupled to said PRAVS means; said DOSA means configured to output a digitized, over sampled and averaged (DOSA) video signal;
    a programmable control and signal processing (PCSP) means coupled to said DOSA means; said PCSP means configured to generate a control signal configured to control an over sampling rate of said DOSA means; said PCSP means configured to process said DOSA video signal; and configured to output said processed DOSA video signal to an output network interface; and
    a power supply selected from the group consisting of: a rechargeable battery, a large capacitor including a charger; and a Low Voltage Dropout LDO power supply.

2. The apparatus of claim 1, wherein said intra-oral image sensor further comprises:
    an X-ray sensitive charge-coupled device (CCD) sensor.

3. The apparatus of claim 1, wherein said intra-oral image sensor further comprises:
    an active pixel sensor (APS) array.

4. The apparatus of claim 1 further comprising:
    a Strobe generator coupled to said PCSP means and coupled to said DOSA means; said Strobe generator under programmable control of said PCSP means configured to generate an A/D control signal to control said DOSA means.

5. The apparatus of claim 4 further comprising:
    a clock drivers block coupled to said Strobe generator and coupled to said sensor; wherein said clock drivers block controlled by clock drivers control signal is configured to output a plurality of clock signals selected from the group consisting of: a reset clock signal; a summing gate clock signal; horizontal clock signals; vertical clock signals; and a transfer clock signal; said clock drivers control signal being generated by said Strobe generator; said plurality of clock signals being used to control said sensor.

6. The apparatus of claim 1, wherein said PRAVS means for processing said raw analog video signal for optimum detection further comprises:
    a trans impedance amplifier block configured to level shift an amplitude of said raw analog video signal to an optimum voltage level range;
    and
    a dual sample & hold (S/H) block including an analog subtractor block; wherein a first sample and hold ($S/H_1$) block is configured to output a video reference signal; wherein a second sample and hold ($S/H_2$) block is configured to output a raw video signal; and wherein said analog subtractor block is configured to subtract said video reference signal from said raw video signal to obtain an adjusted video voltage level.

7. The apparatus of claim 1, wherein said PRAVS means for processing said raw analog video signal for optimum detection further comprises:
    a trans impedance amplifier block configured to level shift an amplitude of said raw analog video signal to an optimum voltage level range;
    and
    a sample & hold (S/H) circuit, wherein a first sample to a S/H block is strobed during a video reference level of a pixel; and wherein a second sample to said S/H block is strobed during a raw video level of said pixel; and wherein each analog sample is digitally converted; and wherein two digital samples are digitally subtracted to obtain an adjusted video level.

8. The apparatus of claim 1, wherein said DOSA means for digitizing, over sampling, and averaging said optimized analog video signal further comprises:
    an A/D converter configured to output the digitized, over sampled and averaged (DOSA) video signal under control of an A/D control signal.

9. The apparatus of claim 1, wherein said PCSP means further comprises:
    a noise shaper block further comprising a noise shaper algorithm configured to attenuate non-linearities in A/D quantization steps, and configured to minimize Integrated Non-Linearity (INL) & Differential Non-Linearity (DNL) of said DOSA video signal.

10. The apparatus of claim 9, wherein said noise shaper block further comprises:
    a non-Gaussian digital noise block configured to add a non-Gaussian digital noise to dither digital steps and to minimize quantization errors in said processed DOSA video signal.

11. The apparatus of claim 1 further comprising:
    an X-ray detector block coupled to said PCSP means, said X-ray detector block performing X-ray detection to filter out a false detection caused by noise; said X-ray detector block configured to output a real video signal indicative of a real X-ray detection.

12. The apparatus of claim 1 further comprising:
    a compression and buffer block coupled to an X-ray detector block; said compression and buffer block configured to compress, to store, and to output a real processed video signal to an output network interface selected from the group consisting of: {a low speed output network interface; and a high speed output network interface}; wherein said low speed output network interface is selected from the group consisting of: {10 mbps Ethernet; USB 1.0; USB 2.0; USB 2.1; and USB 2.2}; and wherein said high speed output network interface is selected from the group consisting of: {100 mbps Ethernet; Gigabit Ethernet; USB 2.0; USB 2.1; USB 2.2; Express Bus; and PCMCIA}.

13. A method of digital dental imaging comprising:
(A) obtaining an intra-oral image by using an intra-oral image sensor; said intra-oral image sensor configured to output a raw analog video signal, said raw analog video signal including said intra-oral image;
(B) processing said raw analog video signal for optimum detection by using a means for processing said raw analog video signal (PRAVS); said PRAVS means configured to output an optimized analog video signal;
(C) digitizing, over sampling, and averaging said optimized analog video signal by using a digitizing, over sampling, and averaging (DOSA) means; said DOSA means configured to output a digitized, over sampled and averaged (DOSA) video signal;
(D) processing said DOSA video signal by using a programmable control and signal processing (PCSP) means; said PCSP means configured to generate a control signal configured to control an over sampling rate of said DOSA means; said PCSP means configured to output said processed DOSA video signal to an output network interface;
(E) generating an A/D control signal to control said DOSA means by using a Strobe generator under programmable control of said PCSP means;
and
(E1) applying a power supply selected from the group consisting of: a rechargeable battery, a large capacitor including a charger; and a Low Voltage Dropout LDO power supply.

14. The method of claim 13, wherein said step (A) further comprises:
(A1) outputting the raw analog video signal including said intra-oral image by using an X-ray sensitive charge-coupled device (CCD) sensor.

15. The method of claim 13, wherein said step (A) further comprises:
(A2) outputting the raw analog video signal including said intra-oral image by using an active pixel sensor (APS) array.

16. The method of claim 13, wherein said step (B) further comprises:
(B1) performing a level shift of an amplitude of said raw analog video signal to an optimum voltage level range by using a trans impedance amplifier block;
(B2) using a first sample and hold (S/H$_1$) block to output a reference video signal that occurs at the beginning of a video pixel readout;
(B3) using a second sample and hold (S/H$_2$) block to output a raw video signal that occurs towards the end of a video pixel;
and
(B4) subtracting said reference video signal from said raw video signal to obtain an adjusted analog reference video voltage level by using an analog subtractor block.

17. The method of claim 13, wherein said step (B) further comprises:

(B5) performing a level shift of an amplitude of said raw analog video signal to an optimum voltage level range by using a trans impedance amplifier block;
(B6) strobing a first sample to a S/H block during a video reference level of a pixel;
(B7) strobing a second sample to said S/H block during a raw video level of said pixel;
(B8) digitally converting each analog sample;
and
(B9) digitally subtracting said two digital samples to obtain an adjusted video level.

18. The method of claim 13, wherein said step (C) further comprises:
(C1) digitizing, over sampling and averaging said a DOSA video signal by using an A/D converter under control of an A/D control signal generated by a Strobe generator.

19. The method of claim 13, wherein said PCSP means further comprises a noise shaper block further comprising a noise shaper algorithm, and wherein said step (D) further comprises:
(D1) processing said DOSA video signal by using said noise shaper block further comprising said noise shaper algorithm.

20. The method of claim 19, wherein said step (D1) further comprises:
(D1, 1) attenuating non-linearities in A/D quantization steps.

21. The method of claim 20, wherein said step (D1) further comprises:
(D1, 2) minimizing Integrated Non-Linearity (INL) & Differential Non-Linearity (DNL) of said DOSA video signal.

22. The method of claim 21, wherein said noise shaper block further comprises a non-Gaussian digital noise block, and wherein said step (D1) further comprises:
(D1, 3) adding a non-Gaussian digital noise to dither digital steps and to minimize quantization errors in said processed DOSA video signal by using said non-Gaussian digital noise block.

23. The method of claim 13 further comprising:
(F) controlling said sensor by a plurality of clock signals generated by a clock drivers block; said clock drivers block being controlled by a clock drivers control signal generated by a Strobe generator; said plurality of clock signals being selected from the group consisting of: {a reset clock signal; a summing gate clock signal; horizontal clock signals; vertical clock signals; and a transfer clock signal}.

24. The method of claim 13 further comprising:
(G) performing X-ray detection to filter out a false detection caused by noise by using an X-ray detector block;
and
(H) outputting a real video signal indicative of a real X-ray detection by using said X-ray detector block.

25. The method of claim 24 further comprising:
(I) compressing, storing, and outputting a real processed video signal to an output network interface by using a compression and buffer block, wherein said output network interface is selected from the group consisting of: {a low speed output network interface; and a high speed output network interface}; wherein said low speed output network interface is selected from the group consisting of: {10 mbps Ethernet; and USB1.0}; and wherein said high speed output network interface is selected from the group consisting of: {100 mbps Ethernet; Gigabit Ethernet; USB2.0; Express Bus; and PCMCIA}.

26. The method of claim 13 further comprising:

(K) transferring a plurality of images to a recipient selected from the group consisting of: {dentists; physicians; insurers; and storage systems} by using said output network interface; wherein said output network interface is selected from the group consisting of: {a low speed output network interface; and a high speed output network interface}; and wherein said low speed output network interface is selected from the group consisting of: {10 mbps Ethernet; and USB1.0}; and wherein said high speed output network interface is selected from the group consisting of: {100 mbps Ethernet; Gigabit Ethernet; USB2.0; Express Bus; and PCMCIA}.

* * * * *